United States Patent
Hsieh et al.

(10) Patent No.: US 10,376,235 B2
(45) Date of Patent: Aug. 13, 2019

(54) NEEDLE GUIDE SYSTEM AND MEDICAL INTERVENTION SYSTEM

(71) Applicants: Industrial Technology Research Institute, Hsinchu (TW); National Taiwan University Hospital, Taipei (TW)

(72) Inventors: Wan-Hsin Hsieh, Taoyuan (TW); Hui-Hsin Lu, New Taipei (TW); Chih-Yuan Wang, Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 348 days.

(21) Appl. No.: 15/385,877

(22) Filed: Dec. 21, 2016

(65) Prior Publication Data

US 2018/0168537 A1    Jun. 21, 2018

(51) Int. Cl.
    *A61B 8/08*    (2006.01)
    *A61B 5/06*    (2006.01)
    *A61B 8/00*    (2006.01)

(52) U.S. Cl.
    CPC .......... *A61B 8/0841* (2013.01); *A61B 8/4254* (2013.01); *A61B 8/4263* (2013.01);
    (Continued)

(58) Field of Classification Search
    None
    See application file for complete search history.

(56) References Cited

U.S. PATENT DOCUMENTS

| 5,647,373 A | 7/1997 | Paltieli |
| 5,953,683 A | 9/1999 | Hansen et al. |

(Continued)

FOREIGN PATENT DOCUMENTS

| TW | 557210 | 10/2003 |
| TW | M514830 | 1/2016 |
| WO | 199927837 | 6/1999 |

OTHER PUBLICATIONS

"Notice of Allowance of Taiwan Counterpart Application," dated Jun. 2, 2017, p. 1-5, in which the listed references were cited.

(Continued)

*Primary Examiner* — Brian T Gedeon
(74) *Attorney, Agent, or Firm* — JCIPRNET

(57) ABSTRACT

A needle guide system is provided. The needle guide system includes a puncture device, an ultrasound transducer, a first orientation detector, a second orientation detector, a proximity detector and a processor. The ultrasound transducer is configured to obtain an ultrasound image. The first orientation detector is disposed on the puncture device, and the second orientation detector is disposed on the ultrasound transducer. The proximity detector is disposed on at least one of the puncture device and the ultrasound transducer, configured to obtain a relative distance between the puncture device and the ultrasound transducer. The processor is configured to obtain a spatial relationship between the puncture device and the ultrasound transducer by using the first orientation detector, the second orientation detector, and the proximity detector, and predict a trajectory of the puncture device in the ultrasound image according to the spatial relationship. In addition, a medical intervention system is also provided.

10 Claims, 5 Drawing Sheets

(52) U.S. Cl.
CPC ............ *A61B 8/4427* (2013.01); *A61B 8/461* (2013.01); *A61B 8/5215* (2013.01); *A61B 5/065* (2013.01); *A61B 5/067* (2013.01); *A61B 2562/0219* (2013.01)

(56) References Cited

U.S. PATENT DOCUMENTS

| | | | |
|---|---|---|---|
| 6,122,538 | A | 9/2000 | Sliwa, Jr. et al. |
| 6,216,029 | B1 | 4/2001 | Paltieli |
| 6,288,785 | B1 | 9/2001 | Frantz et al. |
| 6,604,404 | B2 | 8/2003 | Paltieli et al. |
| 6,611,141 | B1 | 8/2003 | Schulz et al. |
| 6,626,832 | B1 | 9/2003 | Paltieli et al. |
| 6,968,224 | B2 | 11/2005 | Kessman et al. |
| 8,086,298 | B2 | 12/2011 | Whitmore, III et al. |
| 8,556,815 | B2 * | 10/2013 | Pelissier ............ A61B 8/0833 600/443 |
| 2003/0163142 | A1 | 8/2003 | Paltieli et al. |
| 2008/0167621 | A1 | 7/2008 | Wagner et al. |
| 2009/0221908 | A1 * | 9/2009 | Glossop ............ A61B 17/3403 600/424 |
| 2012/0016316 | A1 | 1/2012 | Zhuang et al. |
| 2013/0218024 | A1 | 8/2013 | Boctor et al. |
| 2015/0080710 | A1 | 3/2015 | Henkel et al. |
| 2016/0081653 | A1 * | 3/2016 | Masuda ............ A61B 8/0841 600/424 |

OTHER PUBLICATIONS

Giovanni Turtulici, et al., "Percutaneous Radiofrequency Ablation of Benign Thyroid Nodules Assisted Byavirtual Needle Tracking System", Ultrasound in Medicine & Biology.,vol. 40, No. 7, Jul. 2014, pp. 1447-1452.

Sebastian O.H. Madgwick, "An efficient orientation filter for inertial and inertial/magnetic sensor arrays", Report X-io and University of Bristol, Apr. 2010, pp. 1-32.

Allison Okamura,"Lecture 8:Tracking for surgical navigation",registration, ME 328: Medical Robotics Lecture Note, Apr. 2015, pp. 1-13.

Laura J. Brattain et al.,"Simple and Effective Ultrasound Needle Guidance System",33rd Annual International Conference of the IEEE Engineering in Medicine and Biology Society,Sep. 2011, pp. 8090-8093.

Robinson M. Ferre et al.,"Novel Ultrasound Guidance System for Real-time Central Venous Cannulation: Safety and Efficacy",Western Journal of Emergency Medicine,vol. 15, No. 4, Jul. 2014, pp. 536-540.

Y. Paltieli et al.,"A new guidance system for freehand,obstetric ultrasound-guided procedures",Ultrasound in Obstet & Gynecol, vol. 19, Mar. 2002, pp. 269-273.

Ban C. H. Tsui et al.,"Facilitating Needle Alignment In-Plane to an Ultrasound Beam Using a Portable Laser Unit", Regional Anesthesia and Pain Medicine,vol. 32, No. 1, Jan. 2007, pp. 84-88.

Philipp J. Stolka et al.,"Needle Guidance using Handheld Stereo Vision and Projection for Ultrasound-based Interventions",Medical Image Computing and Computer-Assisted Intervention, 2014, pp. 684-691.

Elena Bergamini et al.,"Estimating Orientation Using Magnetic and Inertial Sensors and Different Sensor Fusion Approaches: Accuracy Assessment in Manual and Locomotion Tasks",Sensors(Basel), vol. 14, Oct. 2014, pp. 18625-18649.

Alfred M. Franz et al.,"Electromagnetic Tracking in Medicine—A Review of Technology, Validation, and Applications", IEEE Transactions on Medical Imaging, vol. 33, No. 8, Aug. 2014, pp. 1702-1725.

* cited by examiner

NEEDLE GUIDE SYSTEM AND MEDICAL INTERVENTION SYSTEM

TECHNICAL FIELD

The disclosure relates to a guide system and a medical system, and particularly relates to a needle guide system and a medical intervention system.

BACKGROUND

When a freehand medical intervention treatment is carried out, an ultrasound image is commonly used to monitor the intervention, so as to reduce injuries to organs and tissues on a needle path as much as possible. For example, when conducting a freehand thyroid nodule biopsy, or carrying out a removal therapy, such as radiofrequency ablation (RFA), on a thyroid nodule or a liver tumor using a needle electrode, the ultrasound image is obtained to indicate the positions of tissues inside the body, so that the user may refer to the ultrasound image and control a needle body accordingly to perform an operation on a target while avoid injuries to nerves or other organs and tissues.

However, before the needle is inserted into the body that is under the field of view of the ultrasound transducer, the ultrasound image is unable to indicate relative positions between the needle body and the tissues inside the body. Hence, it is challenging for the user to determine the preferable position and angle to insert the needle into the body based on the ultrasound image.

SUMMARY

The disclosure provides a needle guide system and a medical intervention system capable of predicting and providing a needle trajectory of a puncture device in an ultrasound image.

A needle guide system according to an embodiment of the disclosure includes a puncture device, an ultrasound transducer, a first orientation detector, a second orientation detector, a proximity detector and a processor. The ultrasound transducer is configured to obtain an ultrasound image. The first orientation detector is disposed on the puncture device, and the second orientation detector is disposed on the ultrasound transducer. The proximity detector is disposed on at least one of the puncture device and the ultrasound transducer and configured to obtain a relative distance between the puncture device and the ultrasound transducer. The processor is coupled to the ultrasound transducer, the first orientation detector, the second orientation detector, and the proximity detector, and configured to obtain a spatial relationship between the puncture device and the ultrasound transducer by using the first orientation detector, the second orientation detector, and the proximity detector, and predict a needle trajectory of the puncture device in the ultrasound image based on the obtained spatial relationship.

A medical intervention system according to an embodiment of the disclosure includes a puncture device, an ultrasound transducer, a first orientation detector, a second orientation detector, a proximity detector, a display device, and a processor. The puncture device is configured to carry out a medical intervention treatment, and the first orientation detector is disposed on the puncture device. The ultrasound transducer is configured to obtain an ultrasound image, and the second orientation detector is disposed on the ultrasound transducer. The proximity detector is disposed on at least one of the puncture device and the ultrasound transducer, configured to obtain a relative distance between the puncture device and the ultrasound transducer. The display device is configured to display the ultrasound image. The processor is coupled to the ultrasound transducer, the first orientation detector, the second orientation detector, the proximity detector, and the display device, and configured to obtain a spatial relationship between the puncture device and the ultrasound transducer by using the first orientation detector, the second orientation detector, and the proximity detector, predict a needle trajectory of the puncture device in the ultrasound image based on the spatial relationship, and display the predicted needle trajectory in the ultrasound image by using the display device.

Based on the above, according to the needle guide system and the medical intervention system of the embodiments of the disclosure, the spatial relationship between the puncture device and the ultrasound transducer is obtained by disposing the first orientation detector and the second orientation detector respectively on the puncture device and the ultrasound transducer, along with the proximity detector disposed on at least one of the puncture device and the ultrasound transducer. Based on the obtained spatial relationship, the needle trajectory of the puncture device in the ultrasound image is predicted.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
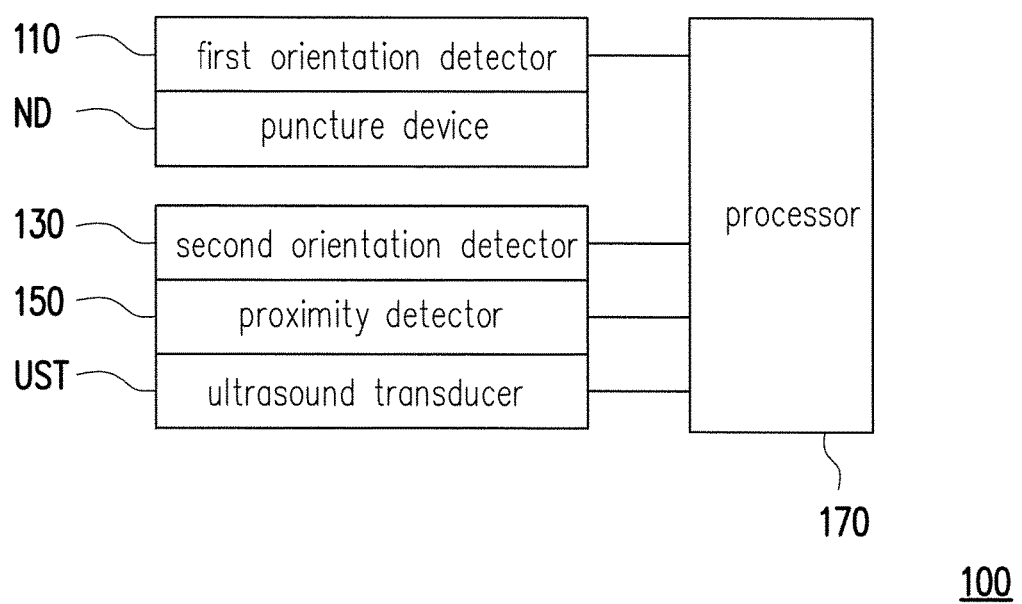
FIG. 1 is a schematic block view illustrating a needle guide system according to an embodiment of the disclosure.

FIG. 1 is a schematic block view illustrating a needle guide system according to an embodiment of the disclosure. Referring to FIG. 1, a needle guide system 100 of the embodiment includes a puncture device ND, an ultrasound transducer UST, a first orientation detector 110, a second orientation detector 130, a proximity detector 150, and a processor 170. The first orientation detector 110 is configured to obtain a first orientation of the first orientation detector 110, and the second orientation detector 130 is configured to obtain a second orientation of the second orientation detector 130. In addition, the first orientation and the second orientation include azimuthal information such as Euler angles. Moreover, the needle guide system 100 of the embodiment also includes the proximity detector 150 configured to measure a distance. The processor 170 is coupled to the first orientation detector 110, the second orientation detector 130, and the proximity detector 150 and receives detection or measurement information from the first orientation detector 110, the second orientation detector 130, and the proximity detector 150. In the needle guide system 100 of the embodiment, the first orientation detector 110, the second orientation detector 130, and the proximity detector 150 may be used with the puncture device ND and the ultrasound transducer UST, for example. In the following, implementation details and use of the respective components of the needle guide system 100 of the embodiment are described in the following as an example.

Figure 2:
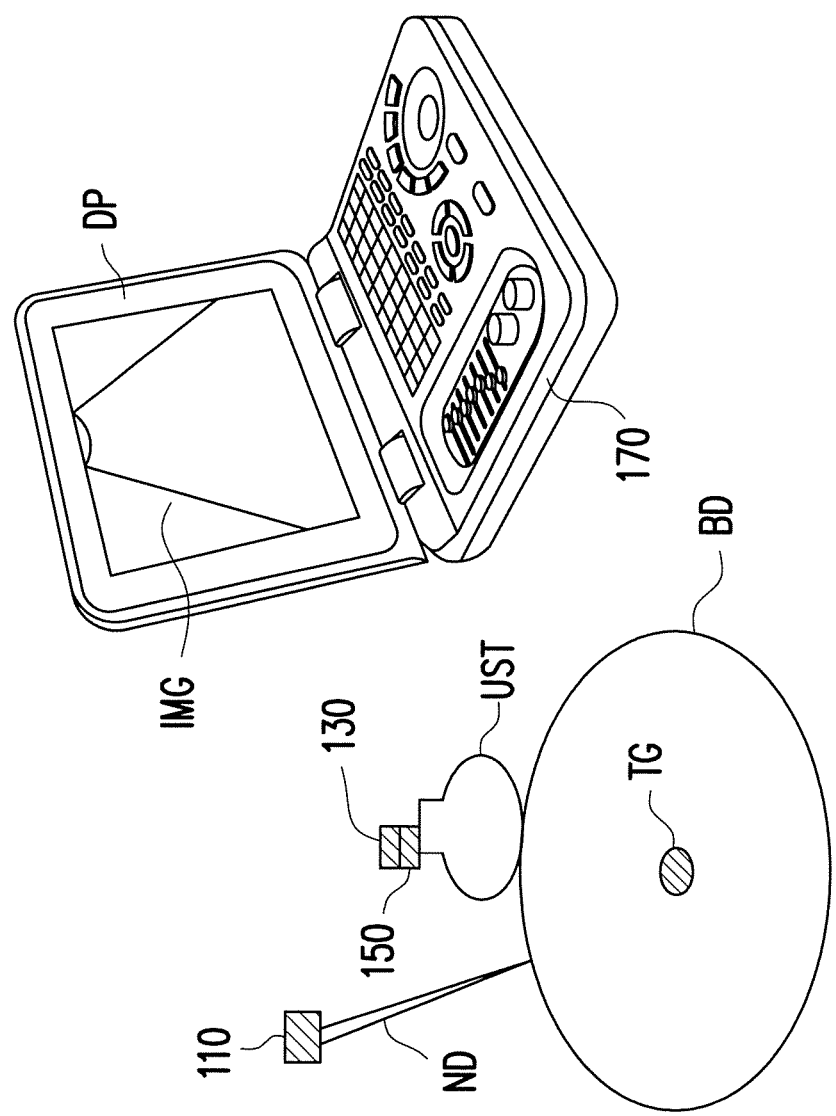
FIG. 2 is a schematic view illustrating a scenario of using a needle guide system according to an embodiment of the disclosure.

FIG. 2 is a schematic view illustrating a scenario of using a needle guide system according to an embodiment of the disclosure. Referring to FIG. 2, in the embodiment, the first orientation detector 110 is disposed on the puncture device ND, for example, and the second orientation detector 130 and the proximity detector 150 are disposed on the ultrasound transducer UST, for example. Accordingly, the processor 170 may obtain a spatial relationship between the puncture device ND and the ultrasound transducer UST by using the first orientation detector 110, the second orientation detector 130, and the proximity detector 150. In the embodiment, the spatial relationship includes the first orientation obtained by the first orientation detector 110, the second orientation obtained by the second orientation detector 130, and a relative distance between the puncture device ND and the ultrasound transducer UST obtained by the proximity detector 150. However, the disclosure is not limited thereto.

It should be noted that the proximity detector 150 is configured to measure the relative distance between the puncture device ND and the ultrasound transducer UST. Therefore, in the embodiment, the proximity detector 150 is disposed on the ultrasound transducer UST. However, it should be understood that the disclosure is not limited thereto. In other embodiments, the proximity detector 150 may also be disposed on the puncture device ND or disposed on the puncture device ND and the ultrasound transducer UST respectively.

In the embodiment, the puncture device ND is a needle for a medical purpose, for example, and may be configured to pierce through a surface of a human body BD to conduct a medical intervention treatment on a target tissue TG, such as biopsy, aspiration, injection, ablation therapy, and electrocauterization, etc. However, the embodiment does not intend to impose a limitation on the type of the puncture device ND of the disclosure. The ultrasound transducer UST is configured to transmit an ultrasound signal toward the human body BD and obtain an ultrasound image IMG based on the ultrasound signal reflected by tissues of the human body BD. In the embodiment, the processor 170 is coupled to a display device DP, and the ultrasound transducer UST is coupled to the processor 170. Thus, the ultrasound image IMG obtained by the ultrasound transducer UST may be displayed on the display device DP.

Before the puncture device ND actually enters a field of view of the ultrasound transducer UST, a relative position between the puncture device ND and the target tissue TG is unable to be observed in the ultrasound image IMG. Therefore, in the embodiment, the processor 170 of the needle guide system 100 may predict a needle trajectory of the puncture device ND in the ultrasound image IMG based on the spatial relationship between the puncture device ND and the ultrasound transducer UST, and display the needle trajectory in the ultrasound image IMG by using the display device DP. In the following, the configuration and use of the respective components of the needle guide system 100 are described in detail.

It should be noted that the disclosure does not intend to impose a limitation on how the respective components are coupled to each other. People having ordinary skills in the art may choose a suitable way based on practical needs. In the embodiment, the processor 170 is coupled to the first orientation detector 110, the second orientation detector 130, the proximity detector 150 and the ultrasound transducer UST through a mini universal serial bus (miniUSB), for example. In other embodiments, the processor 170 may also be coupled to the first orientation detector 110, the second orientation detector 130, the proximity detector 150, and the ultrasound transducer UST through other wired or wireless means.

In the embodiment, the first orientation detector 110 is an inertial measurement unit (IMU), for example, and the inertial measurement unit includes a tri-axial acceleration detector and a tri-axial gyroscope. Specifically, the tri-axial acceleration detector may be configured to detect a direction of gravity acceleration as the basis of reference. With the basis of reference, the tri-axial gyroscope may serve to measure an angular velocity of the first orientation sensor 110. In addition, by integrating the angular velocity with respect of time, variations of Euler angles of the first orientation detector 110 may be obtained. When the first orientation detector 110 is fixedly disposed on the puncture device ND, obtaining the variations of Euler angles of the first orientation detector 110 is equivalent to obtaining variations of Euler angles of the puncture device ND.

Similarly, the second orientation detector 130 is also an inertial measurement unit, for example, and the inertial measurement unit includes a tri-axial acceleration detector and a tri-axial gyroscope. When the second orientation detector 130 is fixedly disposed on the ultrasound transducer UST, obtaining variations of Euler angles of the second orientation detector 130 is equivalent to obtaining variations of Euler angles of the ultrasound transducer UST.

It should be noted that, while the orientation detector is exemplified as an inertial measurement unit including a tri-axial acceleration detector and a tri-axial gyroscope, the disclosure is not limited thereto. In another embodiment, the orientation detector may also be a magnetic, angular rate, and gravity (MARG) detector that further includes a tri-axial magnetic field detector in addition to a tri-axial acceleration detector and a tri-axial gyroscope. By measuring the direction of gravity acceleration using the tri-axial acceleration detector, the tri-axial magnetic field detector may measure a direction of the geomagnetic field, so as to provide a more accurate three-dimensional coordinate system as a reference coordinate system. Thus, errors accumulated by the tri-axial gyroscope during integration may be properly corrected to obtain more accurate variations of Euler angles.

To obtain the spatial relationship between the puncture device ND and the ultrasound transducer UST, the relative distance between the puncture device ND and the ultrasound transducer UST also needs to be measured in addition to respectively measuring the variations of Euler angles. Therefore, the proximity detector 150 is disposed on at least one of the puncture device ND and the ultrasound transducer UST, so as to measure the relative distance between the puncture device ND and the ultrasound transducer UST. For example, the proximity detector 150 may be based on the time-of-flight (TOF) principle, utilize a directional light beam, and receive the light beam reflected by an object to thereby calculate a distance between the proximity detector and the object based on a time-of-flight of a photon. The emitted light beam may be a sound wave or a microwave, for example, and the disclosure does not intend to impose a limitation in this regard. In some embodiments, the proximity detector 150 may further adopt the principle of structured light scanning or triangulation to carry out distance detection.

In the embodiment, the proximity detector 150 and the second orientation detector 130 are disposed on the ultrasound transducer UST. In an embodiment, the second orientation detector 130 and the proximity detector 150 may be integrated into a space detector. By emitting a directional light beam with the proximity detector 150, the relative distance between the ultrasound transducer UST and the puncture device ND becomes measurable.

In the embodiment, the processor 170 is a central processing unit (CPU), for example. However, the disclosure is not limited thereto. In other embodiments, the processor 170 may also be implemented as a system-on-chip (SOC), an application processor, a microprocessor, or other components having a computing capability.

Figure 3:
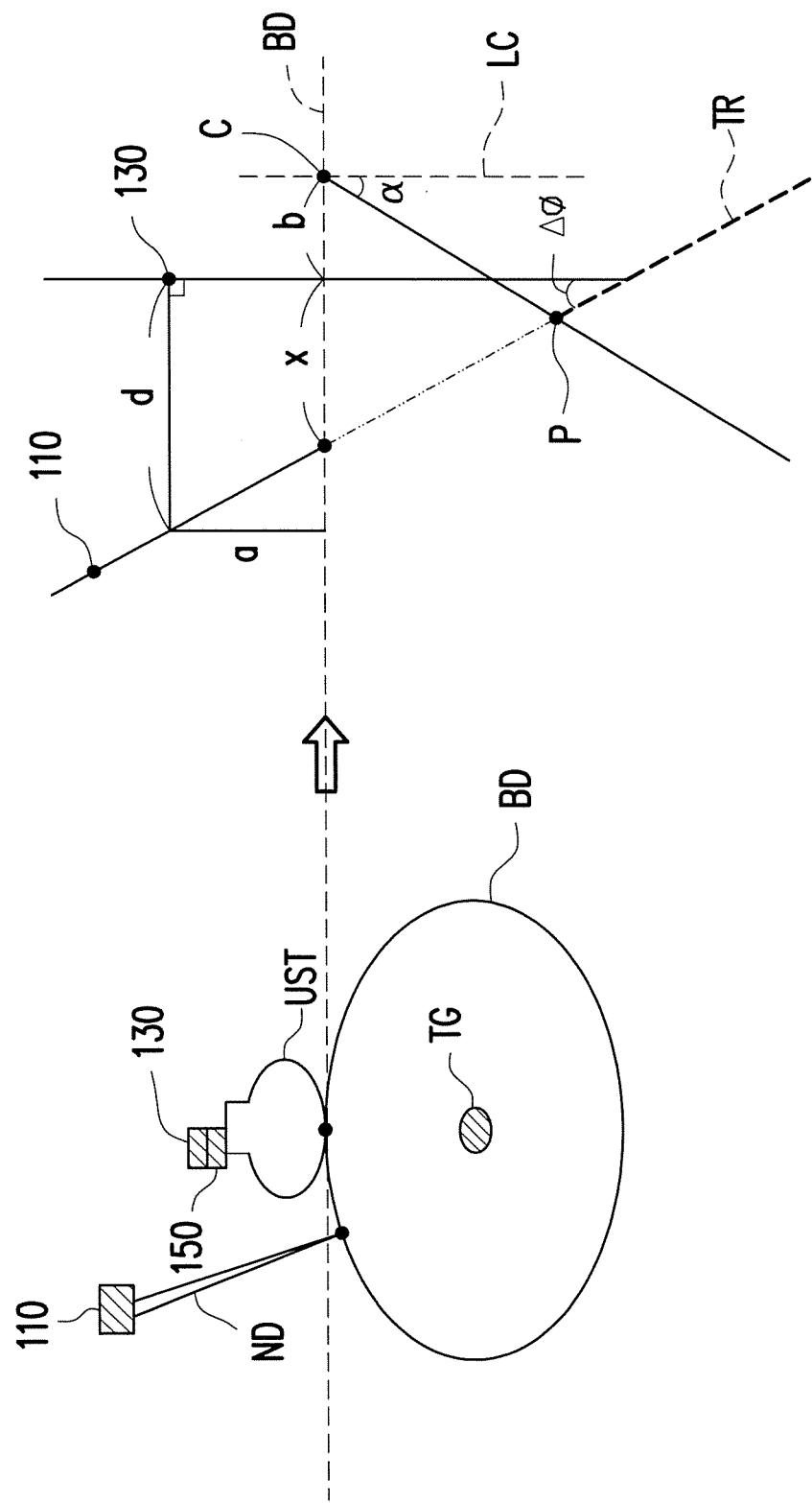
FIG. 3 is a schematic view illustrating a method of predicting a needle trajectory according to an embodiment of the disclosure.

FIG. 3 is a schematic view illustrating a method of predicting a needle trajectory according to an embodiment of the disclosure. In the following, how the needle guide system 100 is used and the method of predicting the needle trajectory of the puncture device ND in the ultrasound image IMG are described with reference to FIG. 3.

In an embodiment, the field of view of the ultrasound transducer UST includes the target tissue TG. In other words, the ultrasound image IMG obtained by the ultrasound transducer UST includes an image of the target tissue TG.

First of all, the orientation detectors, namely the first orientation detector 110 disposed on the puncture device ND and the second orientation detector 130 disposed on the ultrasound transducer UST, are calibrated and zeroing, thus a needle body of the puncture device ND may be ensured to be coplanar with an image plane of the ultrasound image IMG obtained by the ultrasound transducer UST. The procedures of calibration and zeroing facilitate calculation and definition of the first orientation of the first orientation detector 110 and the second orientation of the second orientation detector 130. For example, the variations of Euler angles obtained by the first orientation detector 110 after calibration and zeroing may be readily considered as the first orientation of the first orientation detector 110, and the variations of Euler angles obtained by the second orientation detector 130 after calibration and zeroing may be readily considered as the second orientation of the second orientation detector 130. As another example, after calibration and zeroing, under a circumstance that the second orientation detector 130 remains still, measuring the variations of Euler angles of the first orientation detector 110 is equivalent to obtaining a relative orientation or relative angles between the first orientation detector 110 and the second orientation detector 130.

In the embodiment, the image plane of the ultrasound image IMG is a paper plane, and a line LC is a central line LC of the image plane of the ultrasound image IMG. On the image plane, based on the configuration of the first orientation detector 110, the second orientation detector 130, and the proximity detector 150, a needle guide model shown in FIG. 3 may be obtained. It should be noted that, in the embodiment, the second orientation detector 130 and the proximity detector 150 are integrated into a space detector. Therefore, a position of the second orientation detector 130 shown in FIG. 3 is equivalent to a position of the proximity detector 150.

Referring to FIG. 3, in the embodiment, based on the position of the second orientation detector 130 disposed on the ultrasound transducer UST, parameters a and b may be obtained. In addition, based on the specification of the ultrasound transducer UST, an angle α of field of view of the ultrasound transducer UST may be obtained. Specifically, the parameter a is a height at which the second orientation detector 130 is disposed on the ultrasound transducer UST, and the parameter b is an offset of the second orientation detector 130 disposed on the ultrasound transducer UST with respect to the central line LC of the image plane of the ultrasound image IMG. In another embodiment, the parameter a and the parameter b may also be input by the user based on how the user sets the second orientation detector 130 on the ultrasound transducer UST.

Based on the needle guide model of the embodiment, a position x and an angle $\Delta\phi$ of inserting the puncture device ND determine a needle trajectory TR of the puncture device ND in the ultrasound image IMG. Therefore, in the embodiment, the processor 170 may obtain the angle $\Delta\phi$ by using the orientation detectors, namely the first orientation detector 110 and the second orientation detector 130, and obtaining a relative distance d between the proximity detector 150 and the puncture device ND by using the proximity detector 150. Accordingly, the processor 170 may obtain the position x of the puncture device ND based on Formula (1) in the following, and thus predict the needle trajectory TR of the puncture device ND in the ultrasound image IMG.

$$x = d - a*\tan(|\Delta\phi|) \qquad \text{Formula (1)}$$

It should be noted that, for the ease of description, the proximity detector 150 of the embodiment measures the relative distance d between the ultrasound transducer UST and the puncture device ND in a direction pointing toward the puncture device ND and parallel to a surface of the human body BD. However, the disclosure is not limited thereto. In other embodiments, the proximity detector may also measure a distance by emitting a light beam toward the puncture device ND in other directions not parallel to the surface of the human body BD, and calculating the position x of the puncture device ND based on the direction of the light beam emitted by the proximity detector 150 and trigonometric functions, for example.

In order to predict the needle trajectory TR of the puncture device ND in the ultrasound image IMG, in addition to obtaining the angle $\Delta\phi$ of inserting the puncture device ND, the processor 170 of the embodiment may further determine the needle trajectory TR by calculating a length of a line segment CP. A point C is a point where the central line LC of the image plane and the ultrasound transducer UST or the surface of the human body BD intersect each other, and a point P is a starting point of the predicted needle trajectory TR of the ultrasound image IMG of the puncture device ND. Specifically, the processor 170 may calculate the length of the line segment CP based on the law of sine or Formula (2) in the following.

$$CP = (b+x)*\sin((\pi/2) - |\Delta\phi|)/\sin(\alpha + |\Delta\phi|) \qquad \text{Formula (2)}$$

Accordingly, the processor 170 may predict the needle trajectory TR of the puncture device ND in the ultrasound image IMG based on the angle $\Delta\phi$ of inserting the puncture device ND and the length of the line segment CP. The embodiment of FIG. 3 is described herein for an illustrative purpose. In other embodiments, based on practical needs, the needle position x and the length of CP may be calculated according to the angular and distance information by resorting to trigonometric functions. Another possible circumstance is described in the following for an illustrative purpose.

Figure 4:
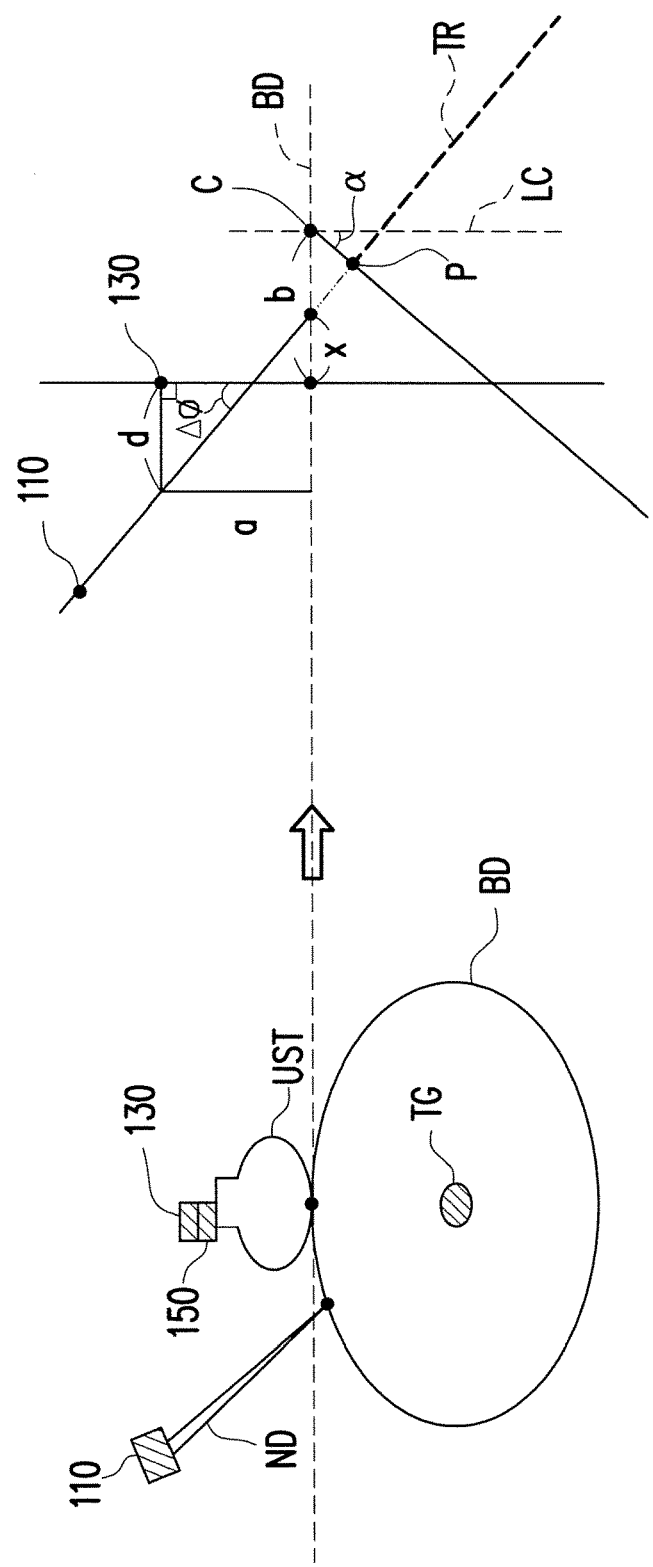
FIG. 4 is a schematic view illustrating a method of predicting a needle trajectory according to another embodiment of the disclosure.

FIG. 4 is a schematic view illustrating a method of predicting a needle trajectory according to another embodiment of the disclosure. In the embodiment, the position x is closer to the ultrasound transducer UST than the position x in FIG. 3. Therefore, the formula adopted when the processor 170 calculates the length of the line segment CP is different from that in the embodiment of FIG. 3.

Referring to FIG. 4, in the embodiment, the puncture device ND inserts the needle between the second orientation detector 130 and central line LC of image plane of the ultrasound image IMG. The processor 170 may obtain the position x of inserting the puncture device ND based on Formula (3) in the following, and thus predict the needle trajectory TR of the puncture device ND in the ultrasound image IMG.

$$x = a*\tan(\oplus\Delta\phi|) - d \qquad \text{Formula (3)}$$

After obtaining the position x, the processor 170 may calculate the length of the line segment CP based on the law of sine or Formula (4) in the following.

$$CP = (b-x)*\sin((\pi/2) - |\Delta\phi|)/\sin(\alpha + |\Delta\phi|) \qquad \text{Formula (4)}$$

Accordingly, the processor 170 may predict the needle trajectory TR of the puncture device ND in the ultrasound image IMG based on the angle $\Delta\phi$ of the puncture device ND and the length of the line segment CP.

It should be noted that, in the previous embodiment, the processor 170 may choose to use Formulae (1) and (2) or Formulae (3) and (4) to calculate the length of the line segment CP based on the relative distance d between the ultrasound transducer UST and the puncture device ND and the angle $\Delta\phi$ of the puncture device ND. However, in some embodiments, the formula adopted by the processor 170 to calculate the processor 170 may also be stored in advance in the processor 170 by the user, for example. Alternatively, the user may choose to calculate based on Formulae (1) and (2) or (3) and (4) when using. In other words, the disclosure does not intend to limit the particulars and steps of calculation. People having ordinary skills in the art may calculate the length of the line segment CP based on known parameters according to their knowledge to plane geometries.

Figure 5:
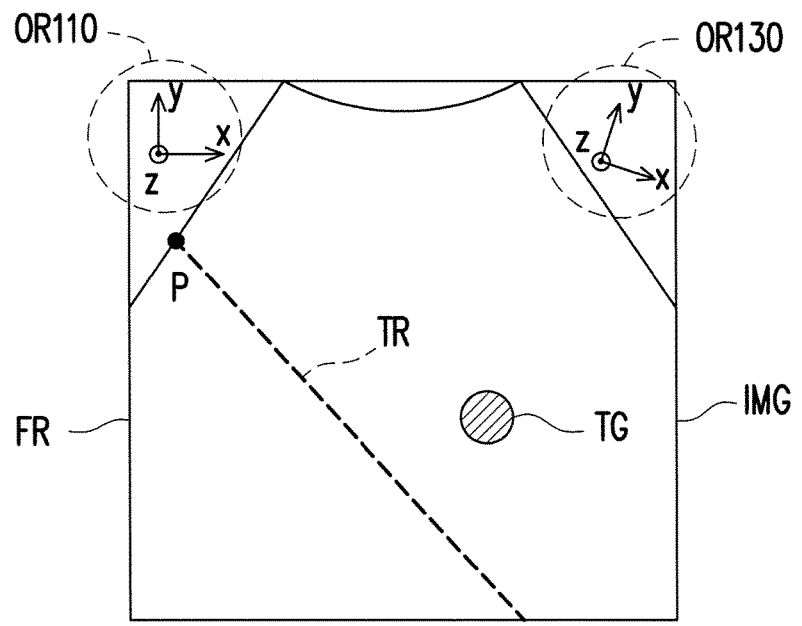
FIG. 5 is a schematic view illustrating an ultrasound image displayed by a display device according to an embodiment of the disclosure.

FIG. 5 is a schematic view illustrating an ultrasound image displayed by a display device according to an embodiment of the disclosure. Referring to FIG. 5, in the embodiment, the ultrasound image IMG obtained by the ultrasound transducer UST may be displayed in the display device DP. Particularly, the needle guide system 100 of the embodiment may further display the predicted needle trajectory TR in the ultrasound image IMG.

It should be noted that, when operating the puncture device ND, the distance between the puncture device ND and the ultrasound transducer UST and the angle $\Delta\phi$ of the puncture device ND may arbitrarily change. With the needle guide system 100 of the embodiment of the disclosure, by using the first orientation detector 110 disposed on the puncture device ND and the second orientation detector 130 and the proximity detector 150 disposed on the ultrasound transducer UST, the processor 170 is able to predict the needle trajectory TR of the puncture device ND in the ultrasound image IMG in a real-time manner, and synchronously display the needle trajectory TR in the ultrasound image IMG.

Besides, in order to keep the needle body of the puncture device ND and the image plane of the ultrasound image IMG coplanar during the operation, the processor 170 may further display a first orientation OR110 of the first orientation detector 110 and a second orientation OR130 of the second orientation detector 130 in the display device DP, so as to represent the spatial relationship between the puncture device ND and the ultrasound transducer UST. Specifically, the first orientation OR110 and the second orientation OR130 may serve to represent relative angles between the puncture device ND and the ultrasound transducer UST.

In the embodiment, the ultrasound image IMG includes the first orientation OR110 of the first orientation detector 110 and the second orientation OR130 of the second orientation detector 130, so as to represent the spatial relationship between the puncture device ND and the ultrasound transducer UST. As shown in FIG. 5, after the procedure of calibration and zeroing, Z-axes of the first orientation OR110 and the second orientation OR130 point away from the image plane (i.e., the xy plane) perpendicularly, for example, indicating that the needle body of the puncture device ND is coplanar with the image plane of the ultrasound image IMG.

In the embodiment, the processor 170 may determine whether the puncture device ND is coplanar with the image plane of the ultrasound image IMG based on the angular information between the puncture device ND and the ultrasound transducer UST obtained by using the first orientation detector 110 and the second orientation transducer 130, and display a result of determination in the display device DP. For example, when the Z-axis direction of the orientation OR110 and the Z-axis direction of the orientation OR130 are parallel to each other and point away from the image plane perpendicularly, a frame FR of the ultrasound image is displayed in green. Alternatively, when the Z-axis direction of the orientation OR110 is deviated from the Z-axis direction of the orientation OR130 and do not point away from the image plane perpendicularly, the frame FR of the ultrasound image is displayed in gray. However, the disclosure is not limited thereto. The processor 170 may also display the result of determination in the display device DP in another way, such as a notification tone, a notification lighting signal, or a vibration signal, etc.

Figure 6:
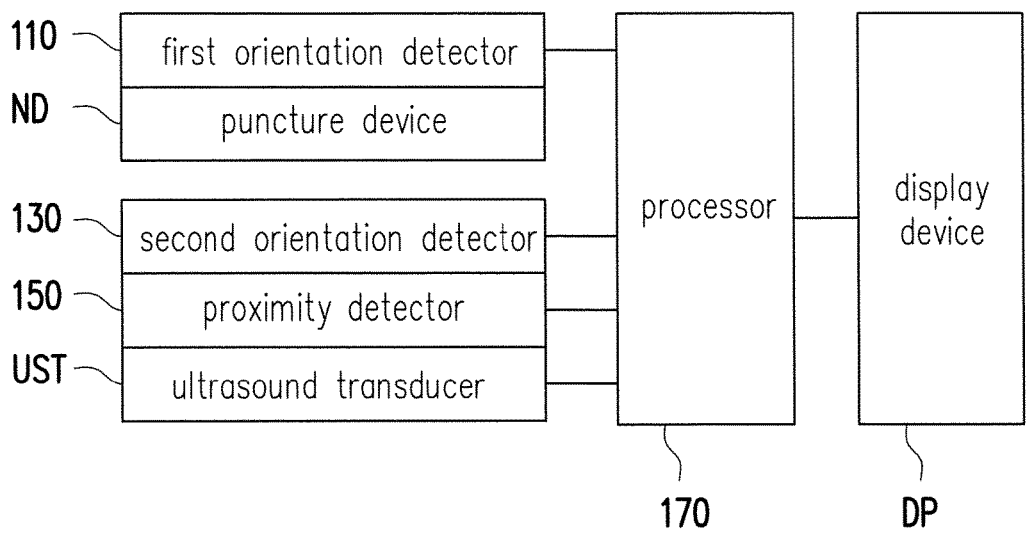
FIG. 6 is a schematic block view illustrating a medical intervention system according to an embodiment of the disclosure.

FIG. 6 is a schematic block view illustrating a medical intervention system according to an embodiment of the disclosure. As shown in FIG. 6, in an embodiment, the needle guide system 100 may be integrated with the display device DP into a medical intervention system 600. In the medical intervention system 600, the first orientation detector 110 is disposed on the puncture device ND, the second orientation detector 130 is disposed on the ultrasound transducer UST, and the proximity detector 150 is disposed on at least one of the puncture device ND and the ultrasound transducer UST. The processor 170 is coupled to the ultrasound transducer UST, the first orientation detector 110, the second orientation detector 130, the proximity detector 150, and the display device DP, and is configured to display the predicted needle trajectory of the puncture device ND in the ultrasound image IMG in the display device DP. Implementation details and use of the respective components of the medical intervention system 600 are similar to those described in the embodiments of FIGS. 1 to 5, and are thus not repeated in the following.

Accordingly, with the needle guide system 100 and the medical intervention system 600 according to the embodiments, the user may operate the puncture device ND and simultaneously refer to the predicted needle trajectory TR of the puncture device ND in the ultrasound image IMG.

In view of the foregoing, according to the needle guide system and the medical intervention system of the embodiments of the disclosure, the spatial relationship between the puncture device and the ultrasound transducer is obtained by disposing the first orientation detector and the second orientation detector respectively on the puncture device and the ultrasound transducer, along with the proximity detector disposed on at least one of the puncture device and the ultrasound transducer. Based on the obtained spatial relationship, the needle trajectory of the puncture device in the ultrasound image is predicted. Besides, in the embodiments of the disclosure, the spatial relationship between the puncture device and the ultrasound transducer is further displayed in the display device. Accordingly, convenient and real-time guidance is available when a medical intervention treatment is carried out.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A needle guide system, comprising:
   a puncture device;
   an ultrasound transducer, configured to obtain an ultrasound image;
   a first orientation detector, disposed on the puncture device;
   a second orientation detector, disposed on the ultrasound transducer;
   a proximity detector, disposed on at least one of the puncture device and the ultrasound transducer and configured to obtain a relative distance between the puncture device and the ultrasound transducer; and
   a processor, coupled to the ultrasound transducer, the first orientation detector, the second orientation detector, and the proximity detector, and configured to:
   obtain a spatial relationship between the puncture device and the ultrasound transducer by using the first orientation detector, the second orientation detector, and the proximity detector, comprising:
      obtaining a first orientation from the first orientation detector and a second orientation from the second orientation detector; and
      calculating a position of inserting the puncture device relative to the ultrasound probe on a body surface by using the relative distance; and
   predict a needle trajectory of the puncture device in the ultrasound image based on the first orientation, the second orientation and the position of inserting the puncture device on the body surface.

2. The needle guide system as claimed in claim 1, wherein the spatial relationship comprises the first orientation, the second orientation, and the relative distance.

3. The needle guide system as claimed in claim 1, wherein the processor is further coupled to a display device, the display device displays the ultrasound image, and the needle trajectory predicted by the processor is displayed in the ultrasound image.

4. The needle guide system as claimed in claim 3, wherein the processor further displays the spatial relationship between the puncture device and the ultrasound transducer by using the display device.

5. The needle guide system as claimed in claim 4, wherein when the processor displays the spatial relationship between the puncture device and the ultrasound transducer by using the display device, the first orientation of the first orientation detector and the second orientation of the second orientation detector are displayed.

6. The needle guide system as claimed in claim 4, wherein the processor determines whether the puncture device and an image plane of the ultrasound image are coplanar, and displays a result of determination in the display device.

7. The needle guide system as claimed in claim 1, wherein each of the first orientation detector and the second orientation detector comprises a tri-axial acceleration detector and a tri-axial gyroscope.

8. The needle guide system as claimed in claim 1, wherein each of the first orientation detector and the second orientation detector comprises a tri-axial acceleration detector, a tri-axial magnetic field detector, and a tri-axial gyroscope.

9. A medical intervention system, comprising:
   a puncture device, configured to carry out a medical intervention treatment;
   an ultrasound transducer, configured to obtain an ultrasound image;
   a first orientation detector, disposed on the puncture device;
   a second orientation detector, disposed on the ultrasound transducer;
   a proximity detector, disposed on at least one of the puncture device and the ultrasound transducer and configured to obtain a relative distance between the puncture device and the ultrasound transducer;
   a display device, configured to display the ultrasound image; and
   a processor, coupled to the ultrasound transducer, the first orientation detector, the second orientation detector, the proximity detector, and the display device, and configured to:
   obtain a spatial relationship between the puncture device and the ultrasound transducer by using the first orientation detector, the second orientation detector, and the proximity detector, comprising:
      obtaining a first orientation from the first orientation detector and a second orientation from the second orientation detector; and
      calculating a position of inserting the puncture device relative to the ultrasound probe on a body surface by using the relative distance;
   predict a needle trajectory of the puncture device in the ultrasound image based on the first orientation, the second orientation and the position of inserting the puncture device on the body surface, and
   display the predicted needle trajectory in the ultrasound image by using the display device.

10. The medical intervention system as claimed in claim 9, wherein the spatial relationship comprises the first orientation, the second orientation, and the relative distance.

* * * * *